United States Patent [19]

Kane et al.

[11] 4,058,572
[45] Nov. 15, 1977

[54] HYDROGENATION OF CYCLIC UNSATURATED COMPOUNDS

[75] Inventors: Bernard J. Kane, Atlantic Beach; Karen E. Irving, Orange Park; James O. Bledsoe, Jr., Jacksonville; Levy A. Canova, Orange Park, all of Fla.

[73] Assignee: SCM Corporation, New York, N.Y.

[21] Appl. No.: 574,911

[22] Filed: May 6, 1975

Related U.S. Application Data

[63] Continuation-in-part of Ser. No. 488,487, July 15, 1974, abandoned.

[51] Int. Cl.$^2$ .................. C07C 29/00; C07C 35/08
[52] U.S. Cl. .......................... 260/631.5; 260/617 C; 260/631 H
[58] Field of Search ............ 260/631 R, 617 H, 631.5, 260/617 C; 252/477 Q

[56] References Cited

U.S. PATENT DOCUMENTS 3,028,418  4/1962  Webb .............................. 260/631 R

OTHER PUBLICATIONS

Pattison, et al., J.A.C.S., vol. 73, pp. 611-613, (1951).

Eliel, Stereochemistry of Carbon Compounds, pp. 434-446, (1962).
Smith, J.A.C.S., vol. 72, pp. 3454-3458, (1950).
Mitsui et al., Chem. & Ind., vol. 1967, pp. 1746-1747.
Tyman et al., Tetrahedron Letters, No. 20, pp. 1773-1775, (1973).

*Primary Examiner*—James O. Thomas, Jr.
*Assistant Examiner*—James H. Reamer
*Attorney, Agent, or Firm*—Richard H. Thomas

[57] ABSTRACT

In a process for hydrogenation, with elemental hydrogen gas in the presence of a hydrogenation catalyst, of a cyclic unsaturated compound having an hydroxyl group projecting from an asymmetric center of the ring and an olefinic carbon-to-carbon double bond which when saturated in the hydrogenation process creates an additional asymmetric center in the ring, the improvement for obtaining increased stereoselectivity by increasing the addition of said hydrogen to that side of the olefin bond on the same side of the compound molecule as said hydroxyl group, comprising: conducting said hydrogenation with a nickel hydrogenation catalyst that has a substantial fraction of its reactive surfaces inactivated.

The invention is particularly applicable to the hydrogenation of d-trans-piperitol to d-isomenthol.

13 Claims, No Drawings

HYDROGENATION OF CYCLIC UNSATURATED COMPOUNDS

This application is a continuation-in-part of prior application Ser. No. 488,487, filed July 15, 1974, now abandoned by Bernard J. Kane et al and assigned to assignee of the present application.

The present invention relates to the stereoselective hydrogenation of cyclic unsaturated compounds. The invention is particularly applicable to the stereoselective hydrogenation of terpene monocyclic allylic alcohols and will be described with reference to the hydrogenation of d-trans-piperitol to d-isomethol, although it will be apparent to those skilled in the art that the invention has broader application.

BACKGROUND OF THE INVENTION

Stereoselectivity is a concept described in the literature. Essentially it means that synthesis that produces one diastereoisomer (or diastereoisomeric dl pair) of a given structure in considerable predominance over all other possible diastereoisomers (or diastereoisomeric dl pair) of the same structure. Reference can be had to *Stereochemistry of Carbon Compounds*, E. L. Eliel, 1962, chapter 15, pages 434–446, McGraw-Hill, the subject matter of which is incorporated by reference herein.

A principal value of d-trans-piperitol is as an intermediate to d-isomethol by hydrogenation. d-Isomenthol is an important product since it is readily isomerized to l-menthol which in turn is an important flavoring or cooling ingredient for pharmaceuticals and other products.

The hydrogenation of d-trans-piperitol to d-isomenthol and related hydrogenation processes have been known for many years and are disclosed in the following publications:

1. "Synthesis of Laevo-menthol from a Citrus By-Product," J. C. Leffingwell and R. E. Shackelford, presented by Dr. Leffingwell at the annual Tobacco Research Chemists' Conference, Winston-Salem, North Carolina, on Oct. 5, 1973;
2. "Menthol, Part 4: Manufacturing Processes and Syntheses," by Dr. Siegfried Mignat and Fredrich Porsch, Dragoco Report, 1962, No. 1, 10–23 (Page 17);
3. "Reactions of Alpha, Beta-Unsaturated Cyclic Aldehydes and Ketones Part IX," A. Killen Macbeth and J. S. Shannon, *Journal of the Chemical Society*, 1952, 2852–2856;
4. "Reactions of Alpha, Beta-Unsaturated Cyclic Aldehydes and Ketones Part XI," A. Killen Macbeth, B. Milligan and J. S. Shannon, *Journal of the Chemical Society*, 1953, 901–902;
5. U.S. Pat. No. 3,028,418, Example No. 22 by Robert L. Webb;
6. U.S. Pat. No. 2,894,040 by Joseph P. Bain et al;
7. U.S. Pat. No. 2,935,526 by Joseph P. Bain.

The hydrogenation of d-trans-piperitol and such other related processes are representative of stereoselective syntheses wherein one diasteroisomer is produced in considerable predominance over other diastereoisomers. However, typically the stereoselectivity is not complete.

Although good yields of d-isomenthol are reported in the prior art, virtually all of the prior art work was carried out before vapor phase chromatograhy was available for analysis. Reported selectivities of up to 95% of d-isomenthol as determined by infrared analysis are thus open to question.

Applicants' own experience with the conventional hydrogenation of d-trans-piperitol is that it produces in addition to the desired d-isomenthol, an amount of the isomeric d-menthol,[1] as shown in the following equation:

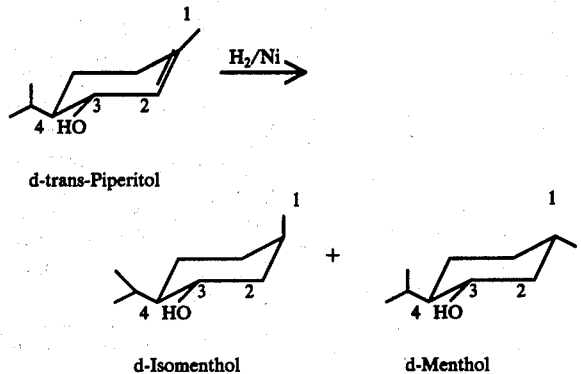

[1] It has been determined that there are actually either isomers of menthol; 1-isomenthol, 1-neoisomenthol, d-menthol, 1-neomenthol, d-isomenthol, d-neoisomenthol, 1-menthol and d-neomenthol. The prefixes d- and 1- refer to optical rotatory power of each substance and do not indicate relative configurations. Thus, 1-menthol is configurationally related to d-iso, d-neo and d-neoisomenthols. The prefix "iso" means that the methyl group is in the axial position, and the prefix "neo-" means that the hydroxyl group is in an axial position (as compared to equatorial positions). A good discussion of the menthols can be found in the publication The Terpenes, Vol. 1, part 1, chapter 2, pages 230–250, by J. L. Simonsen, Cambridge at the University Press, 1947. The difference between the d-isomenthol and d-menthol is in the position of the methyl group relative to the positions of the hydroxyl and isopropyl groups of the molecule. Namely, in d-isomenthol, the methyl group is in an axial position, the hydroxyl group being equatorial, whereas in d-menthol, both the methyl and hydroxyl groups are equatorial. The isopropyl group by reason of its steric size exists almost exclusively in the equatorial position.

This preferential but incomplete stereoselective hydrogenation of cyclic allylic alcohols has also been observed by S. Mitsui et al, as reported in *Chemistry and Industry*, Oct. 14, 1967 (1746–1747). Using 3-methylcyclohex-2-enol, they found that, over Raney nickel, hydrogen tended to attack from the same side of the double bond as the hydroxyl group[2] to give stereoselectively the trans-isomer, as compared to production of more cis-isomer over a palladium catalyst. However, as indicated, the stereoselectivity was not complete, and they reported a percentage yield in the product of only 87% of the trans-isomer.

[2] In the stereoselective synthesis of d-isomenthol, referring to the above equation, it is surmised, as in Mitsui et al, that there is a preferential attack by hydrogen from the same side of the double bond as the hydroxyl group, forcing the methyl group in the No. 1 position to form an axial bond. Some hydrogen attacks from the opposite side, however, forcing the methyl group to form an equatorial bond with the molecule.

In the above Webb U.S. Pat. No. 3,028,418, in example 22, the stereoselective hydrogenation of piperitols (in this example, d-cis-piperitol and 1-trans-piperitol to neomenthol and isomenthol, respectively) is reported. Webb gives results of 92–95% stereoselectivity, by infrared analysis, although applicants' tests conducted under similar conditions but with d-trans-piperitol, gave a product stereoselectivity of only 89.5%, as determined by vapor phase chromatography.

1-Menthol has to be of very high optical purity to meet U.S. Pharmacopoeia specifications, and the presence of d-menthol seriously lowers the optical purity of 1-menthol. In fact, the presence of d-menthol produces a racemic mixture wherein 5% d-menthol results after further processing in an optical purity of only 90% for 1-menthol. Whereas d-isomenthol is readily isomerized to l-menthol, the d-menthol is not, and is very difficult to separate from d-isomenthol. The presence of d-menthol also has a severe effect in depressing the melting point below specification.

Thus an increase in stereoselectivity of only about 5%, to about 92%, preferably to about 95% or better, in the synthesis of d-isomenthol, is of substantial significance commercially.

A publication of interest with regard to the present invention is entitled: "Some Factors Influencing the Activity of Raney Nickel Catalyst. III. The Poisoning of Raney Nickel by Halogen Compounds," John N. Pattison and Ed. F. Degering, *Journal American Chem. Soc.*, 73, 1951, pages 611–613. Referring in particular to FIG. 1, of the publication, it is shown that a Raney nickel catalyst has surfaces of different reactivity, and that poisoning agents, in this case HCl, react with or block the most reactive surfaces first. Specifically, the Figure shows a distinct break in the effect on hydrogenation reaction rate in the hydrogenation of styrene with additions of more than 0.005 grams HCl. Pattison et al make no mention of the effect of the poisoning on stereoselectivity, nor is the hydrogenation of allylic alcohols or the synthesis of l-menthol mentioned in the article. The sole purpose of the article was to show the effect of catalyst poisoning with halogen compounds on reaction rates.

A similar such disclosure is contained in the publication Annalen Der Chemie, 660, (1962), pages 1–23. This publication describes the relative poisoning of Raney nickel by many compounds as determined by reduction of hydrogenation rate. No reference to stereoselectivity is contained in the publication.

BRIEF SUMMARY OF THE INVENTION

The present invention resides in the discovery that in a process for hydrogenation, with elemental hydrogen in the presence of a hydrogenation catalyst, under hydrogenation conditions, or a cyclic unsaturated compound having an hydroxyl group projecting from an asymmetric center of the compound ring and an olefinic carbon-to-carbon double bond, which when saturated in the hydrogenation process creates an additional asymmetric center in the ring, an increased steroselectivity or increased addition of hydrogen to that side of the olefin bond on the same side of the compound molecule as said hydroxyl group is obtained by conducting the hydrogenation with a nickel containing hydrogenation catalyst that has a substantial fraction of its reactive surface inactivated.

In particular, it has been discovered that a stereoselective synthesis of 92% or better in the hydrogenation of cyclic compounds, as defined, can be obtained.

A particular aspect of the invention resides in the hydrogenation of terpene, cyclic, allylic alcohols wherein the hydroxyl group has a maximum directive affect on the attack of the molecule double bond by hydrogen. The invention is particularly applicable to the hydrogenation of d-trans-piperitol to d-isomenthol.

Examples of other cyclic alcohols which can be stereo-selectively hydrogenated in accordance with the concepts of the present invention includes cis- and trans- isopiperitenols, cis-piperitol, cis- and trans- verbenol, cis- and trans- 3-p-menthene-5-ols, cis- and trans- carveols, cis- and trans- pulegols, cis- and trans- psi-carveol, cis- and trans- 1-menthene-5-ols, 3-methylcyclopent-3-enol, cis- and trans- pinocarveols, cis- and trans- umbellerol, eucarvol and 3-methylcyclopent-2-enol.

The structures of representative such compounds are as follows.

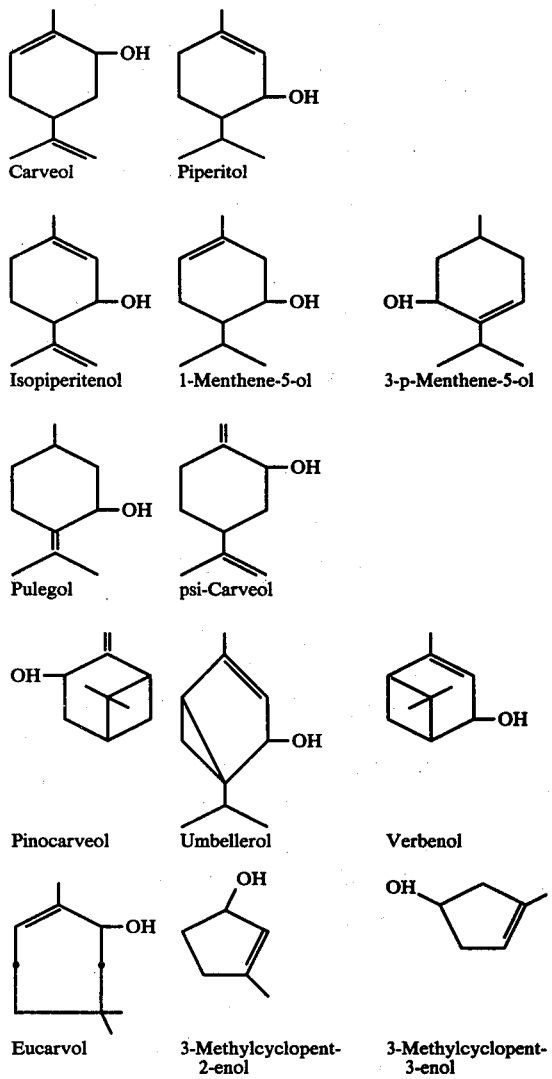

Referring to the above, it should be apparent that in each of the above compounds, the hydroxyl radical projects from an asymmetric center in the ring of the compound. It is also apparent that in all of the shown compounds, a double bond leads to a tertiary carbon atom and its hydrogenation thus results in the formation of a second asymmetric center.

Also, the substituents in the No. 1 and No. 4 positions of the ring need not be methyl and isopropyl groups, as the present invention is applicable independent of the particular substituent or substituents so attached. The compound can be heterocyclic.

As shown above, the hydroxyl or other substituent need not be allylic to the double bond, although as mentioned, this is preferable. The compound in question may be a five, six or seven membered ring compound.

A preferred nickel catalyst for use in the process of the present invention is a Raney nickel catalyst, although it will be apparent from the following disclosure that the invention is applicable to all types of nickel catalysts, supported or of the Raney type. Suitable Raney nickel type catalysts are those marketed by W. R. Grace & Co. under the trademark "Raney 28" and "Raney 30". The term "Raney" is indicated to be a registered trademark of W. R. Grace & Co. However, it is used generically in the art to indicate a class of catalysts, and for purposes of this application it is also so used. Other suitable nickel catalysts of the Raney type include a "sponge" nickel catalyst marketed by Activated Metals Inc., under the trademark "A-5000", and a catalyst prepared in accordance with the procedure set forth in "Organic Syntheses Collective Volume 3", John Wiley & Sons, New York, copyright 1955, page 176. Supported nickel catalysts include Harshaw Chemical Co. "1404 P" nickel catalyst (trademark Harshaw Chemical Co.), which is 68% nickel on a proprietary support; and Girdler's catalyst "G-69" (trademark Girdler Chemical Inc.), a nickel catalyst which is zirconium promoted nickel on Kieselguhr, 55% nickel and 2% zirconium. Others will be apparent to those skilled in the art.

The nickel catalyst can have a portion of its reactive surfaces deactivated by employing any of a large number of catalyst modifiers. A preferred such modifier is a 7.5% aqueous solution of $NiCl_2.6H_2O$, and the treatment of the catalyst is carried out by mixing the solution with the catalyst and stirring the same for a short period of time at room temperature. Hydrogenation is then carried out in the presence of a non-reactive solvent such as isopropanol until hydrogen uptake ceases. The modifying compounds can be organic or inorganic and preferably are selected from the group consisting of: inorganic metal salts from Groups I to VIII (preferably Periods 4 through 7 and the Rare Earths) of the Periodic Table; organic halides of the aliphatic and aromatic types; and non-metallic compounds such as $BF_3.Et_2O$ and $AsCl_3$. Specific such metal salt modifiers include HCl (disclosed by Pattison et al); $AlCl(i-PrO)_2$; and $Al(OH)(OAc)_2$[3]; $CuCl_2$; $Cu(OAc)_2$; $CuSO_4$; $CuBr_2$; $SrCl_2$; $ZnCl_2$; $ZnSO_4$; $Zn(OAc)_2.2H_2O$; $ZnBr_2$; $CdCl_2$; $HgCl_2$; $TiCl_3$; $Ti_2(C_2O_4)_3$; $SnCl_4$; $VBr_3$; $CrCl_3 .6H_2O$; $MoCl_5$; $Mn(OAc)_2.4H_2O$; $MnSO_4.H_2O$; $Fe(OH)(OAc)_2$; $FeBr_3$; $CoCl_2$; $Co(OAc)_2.4H_2O$; $NiSO_4$; $NiCl_2.6H_2O$; $NiBr_2.6H_2O$; $NiI_2.6H_2O$; $RuCl_2$; and $SmCl_3$. Some organic modifiers are: $CH_2Cl_2$; $CHCl_3$; $CCl_4$; $CHBr_3$; $CH_2Br_2$; $CBr_4$; $CBrCl_3$; 3-chlorpropene; 3-bromopropene; trichloroacetic acid; 1,2-dichloroethane; chloroacetone; 2-chloroethanol; chlorobenzene; o-chlorotoluene; p-chlorophenol; p-chloroacetophenone; and benzoyl chloride.

[3] "i-Pro" means the isopropoxy radical; "OAc" means the acetate radical.

The solvent used in the hydrogenation process is not critical as long as it does not poison the catalyst. On this basis, solvents like chloroform and dimethylsulfoxide obviously should not be used. However, suitable solvents include toluene, menthane, acetone, isopropyl alcohol, ethyl alcohol and methyl alcohol. The solvent need not be anhydrous, and in fact, water levels up to about 8% or higher can lead to slightly improved stereoselectivity.

Conventional hydrogenation conditions are employed in the hydrogenation process; for instance with regard to pressure (100 mm absolute to 5000 psig), proportions, temperature (−20° to 150° C.) and time. However, optimum stereoselectivity may be experienced at pressures between atmospheric and 400 psig and temperatures between about 10° to about 85° C., more preferably room temperature (25°–35° C.). For purposes of the present application, the term "hydrogenation conditions" where employed shall mean conventional hydrogenation conditions.

Conventional catalytic amounts of the catalyst for hydrogenation should be employed, e.g., about 0.01–20% catalyst metal, although good results have been experienced with about 1–6% catalyst metal, preferably about 4% catalyst metal by weight, based on the weight of the alcohol, e.g., d-trans-piperitol.

The catalyst modifier may be added directly to the mixture to be hydrogenated instead of pre-treating the catalyst with the modifier. In such cases, the amount of modifier employed may vary from 0.01% to 100% based on the weight of the catalyst. When a solution of the modifier is employed to treat the catalyst, prior to hydrogenation the supernatant solution of the modifier is removed by decantation or other means.

An aspect of the invention resides in the discovery that optimum results are obtained by providing a d-trans-piperitol feed or other alcohol or substrate which is substantially sulfur-free.

Although applicants are not to be held to any particular theory as to the reasons for the improved results achieved in accordance with the present invention, it is believed as taught by Pattison et al that the nickel catalyst has two distinct types of reactive surfaces and that the more reactive surfaces are less selective sites for hydrogenation. It is further believed that the listed modifier compounds tend to deactivate the most reactive surfaces improving the catalyst stereoselectivity. This is confirmed by a detectable decrease in the reaction rate following addition of the modifier. However, the modification of the catalyst is insufficient to render the catalyst inoperative to any significant extent.

An advantage of the invention is that the modified catalyst may be reused in successive hydrogenation reactions two, three or more times.

The invention will become apparent from the following examples. In the examples, it is understood that all percentages or parts are percentages or parts by weight and that temperatures are in degrees Centigrade, unless otherwise stated. Pressure is in pounds per square inch gauge. Time is in hours.

EXAMPLE 1

In this example, for purposes of comparison, hydrogenation was carried out with Raney nickel catalysts which were untreated and treated in accordance with the concepts of the present invention. Treatment of the Raney nickel catalyst (specifically Grace "Raney 28" and "Raney 30") was accomplished by adding 20 milliliters of 7.5% aqueous $NiCl_2.6H_2O$ solution to a 4 gram sample of the catalyst, stirring the mixture for 30 minutes at room temperature and then allowing the catalyst to settle. The supernatant excess liquid was decanted, and the catalyst was washed three times with 35 milliliters of isopropanol.

Hydrogenation was carried out by adding 10 grams of d-trans-piperitol, 10 grams isopropanol, and 0.4 grams catalyst to a Parr Shaker and hen pressurizing the Shaker with hydrogen at various temperatures and pressures until hydrogen uptake ceased. The following results were obtained.

TABLE 1

| Catalyst Treatment | % Cat. | Pres. (Psig) | Temp. C° | % Conv. | d-Men | d-Iso |
|---|---|---|---|---|---|---|
| None | 4 | 60 | 25 | 100 | 13.9 | 86.1 |
| None | 5 | 400 | 28 | 99.9 | 14.3 | 85.6 |
| " | 5 | 400 | 28 | 99.9 | 13.7 | 86.1 |

TABLE 1-continued

| Catalyst Treatment | % Cat. | Pres. (Psig) | Temp. C° | % Conv. | % d-Men | % d-Iso |
|---|---|---|---|---|---|---|
| " | 2 | 400 | 70 | 99.6 | 14.2 | 85.8 |
| 7.5% NiCl₂ | 4 | atm. | 25 | 99.0 | 3.4 | 96.6 |
| " | 4 | 60 | 25 | 97.5 | 2.5 | 97.5 |
| " | 4 | 60 | 50–55 | 100.0 | 4.8 | 95.2 |
| " | 4 | 60 | 65–75 | 100.0 | 6.1 | 93.9 |
| " | 4 | 200 | 25 | 100.0 | 2.9 | 97.1 |

In Table 1, "d-Men" means d-menthol and "d-Iso" means d-isomenthol. "Pres." is the hydrogen pressure and "Temp." is the temperature of the reaction. "Cat." is the catalyst and "Conv." is the piperitol conversion.

It is apparent from the above table that satifactory conversions to the desired d-isomenthol were obtained only with the treated catalyst. Higher temperatures results in lower d-isomenthol stereoselectivity. Pressure levels and time were not critical.

EXAMPLE 2

This example illustrates the ability of a Raney nickel catalyst treated in accordance with the concepts of the present invention to successfully hydrogenate multiple charges of d-trans-piperitol with high conversion and little change in stereoselectivity.

Hydrogenation was carried out with 2,000 grams of d-trans-piperitol, 2,000 grams isopropanol, 80 grams Raney nickel catalyst (Grace No. 30) treated as in Example 1, at 62 psig, 25° C, and 1,000 RPM agitation. The following results were obtained with three successive charges.

TABLE 2

| Charge No. | Reaction Time (Hrs.) | % Conv. | % d-Men | % d-Iso |
|---|---|---|---|---|
| 1 | 2.8 | 99.1 | 4.6 | 95.3 |
| 2 | 5.6 | 100.0 | 4.8 | 95.2 |
| 3 | 5.0 | 97.4 | 4.8 | 95.2 |

EXAMPLE 3

This example illustrates advantages of the invention with the addition of different inorganic modifiers to a "Raney 28" nickel catalyst.

Ten grams d-trans-piperitol, 10 grams isopropanol or other solvent, and 0.4 grams "Raney 28" nickel catalyst were employed. Hydrogenation was carried out at 50–60 psig at room temperature. The following results were obtained.

TABLE 3

| Run | Catalyst₄ Modifier | | Periodic Table Group | Wt. Modifier/ Wt. Catalyst | Solvent | % Conversion | Stereo % Selectivity |
|---|---|---|---|---|---|---|---|
| 1 | HCl | (B) | I | .005 | i-PrOH | 98.2 | 93.4 |
| 2 | CuCl₂ | (B) | I B | .075 | 2-Butanone | 100 | 98.4 |
| 3 | Cu(OAc)₂ | (B) | I B | .250 | i-PrOH | 99 | 94.6 |
| 4 | CuSO₄ | (B) | I B | .250 | " | 98 | 95.8 |
| 5 | CuBr₂ | (B) | I B | .033 | " | 98 | 97.5 |
| 6 | SrCl₂ | (A) | II A | .200 | " | 100 | 92.0 |
| 7 | ZnCl₂ | (B) | II B | .025 | " | 99.8 | 96.1 |
| 8 | ZnSO₄ | (B) | II B | .400 | " | 100 | 96.0 |
| 9 | Zn(OAc)₂ . 2H₂O | (A) | II B | .200 | " | 82 | 95.1 |
| 10 | ZnBr₂ | (A) | II B | .250 | " | 97.7 | 96.4 |
| 11 | CdCl₂ | (A) | II B | .200 | " | 97.8 | 93.0 |
| 12 | HgCl₂ | (B) | II B | .200 | " | 92.6 | 92.9 |
| 13 | BF₃ . Et₂O | (B) | III B | .100 | Toluene | 16.2 | 92.1 |
| 14 | AlCl(i-PrO)₂ | (B) | III B | .100 | i-PrOH | 99.0 | 93.7 |
| 15 | Al(OH) (OAc)₂ | (A) | III B | .100 | " | 100 | 94.0 |
| 16 | TiCl₃ | (B) | IV A | .030 | Toluene | 89.8 | 96.8 |
| 17 | Ti(C₂O₄)₃ . 10H₂O | (B) | IV A | .020 | Toluene | 97.7 | 93.8 |
| 18 | SnCl₄ | (A) | IV B | .200 | i-PrOH | 62.7 | 97.4 |
| 19 | VBr₃ | (A) | V A | .020 | " | 100 | 95.1 |
| 20 | AsCl₃ | (B) | V B | .012 | " | 99.1 | 95.3 |
| 21 | CrCl₃ . 6H₂O | (B) | VI A | .036 | " | 95 | 96.7 |
| 22 | MoCl₅ | (B) | VI A | .100 | " | 84.7 | 96.8 |
| 23 | Mn(OAc)₂ . 4H₂O | (A) | VII A | .200 | " | 99 | 93.3 |
| 24 | MnSO₄ . H₂O | (A) | VII A | .200 | " | 98 | 92.6 |
| 25 | Fe(OH) (OAc)₂ | (B) | VIII | .020 | CH₃OH | 95.9 | 95.7 |
| 26 | FeBr₃ | (B) | VIII | .025 | i-PrOH | 100 | 97.3 |
| 27 | CoCl₂ | (B) | VIII | .019 | " | 96 | 96.8 |
| 28 | Co(OAc)₂ . 4H₂O | (B) | VIII | .200 | " | 100 | 95.6 |
| 29 | NiSO₄ | (A) | VIII | .050 | " | 99 | 95.1 |
| 30 | NiCl₂ . 6H₂O | (A) | VIII | .375 | " | 97.5 | 97.5 |
| 31 | NiBr₂ . 6H₂O | (A) | VIII | .250 | " | 99.9 | 97.5 |
| 32 | NiI₂ . 6H₂O | (A) | VIII | .050 | " | 67.6 | 97.1 |
| 33 | RuCl₂ | (A) | VIII | .020 | " | 87.8 | 92.4 |
| 34 | SmCl₃ | (A) | rare earth | .050 | " | 100 | 93.1 |
| 35 | CuCl | (B) | IB | .013 | " | 97.9 | 92.0 |

⁴The catalyst was modified by one of the two following methods before being used in the hydrogenation.
Method A: The catalyst was stirred for 30 minutes with an aqueous solution of the modifier before decanting the excess solution and washing the catalyst three times with the solvent to be used for the hydrogenation.
Method B: The modifier was added as a solid or in solution to the catalyst in the solvent used for the hydrogenation.

In the above Table, "i-PrOH" means isopropanol. Again, "i-Pro" means an isopropoxy radical, and "OAc" means an acetate radical.

It should be apparent from Table 3 that the inorganic modifiers most suitable towards achieving a high conversion and a stereoselectivity of more than 92% are those metal salts selected from Groups I through VIII, preferably Periods 4 through 7, boron and arsenic compounds, and salts of the Rare Earths. Optimum results were obtained in run No. 6 with CuCl₂. The anion of the salts can be acetate, halide, sulfate, and others.

Selectivity in Table 3 is defined as percent d-isomenthol divided by percent d-isomenthol plus percent d-menthol, times 100.

EXAMPLE 4

The procedure of Example 3 was repeated with a number of organic modifiers, with the following results as shown in Table 4.

TABLE 4

| Run | Catalyst Modifier | Wt. Modifier/ Wt. Catalyst | % Conversion | % Stereo-selectivity |
|---|---|---|---|---|
| 1 | $CH_2Cl_2$ | .200 | 98.0 | 95.6 |
| 2 | $CHCl_3$ | .015 | 100 | 96.4 |
| 3 | $CCl_4$ | .015 | 77.8 | 97.1 |
| 4 | $CHBr_3$ | .016 | 100 | 96.0 |
| 5 | $CH_2Br_2$ | .016 | 100 | 96.7 |
| 6 | $CBr_4$ | .006 | 100 | 92.5 |
| 7 | $CBrCl_3$ | .012 | 99.7 | 95.2 |
| 8 | 3-Chloropropene | .200 | 20.7 | 94.8 |
| 9 | 3-Bromopropene | .050 | 44.0 | 96.4 |
| 10 | Trichloroacetic Acid | .050 | 83.0 | 97.0 |
| 11 | 1,2-Dichloroethane | .013 | 97.8 | 91.6 |
| 12 | Chloroacetone | .050 | 98.1 | 96.0 |
| 13 | 2-Chloroethanol | .200 | 98.3 | 91.2 |
| 14 | Chlorobenzene | .100 | 99.2 | 96.6 |
| 15 | o-Chlorotoluene | .013 | 93.8 | 91.5 |
| 16 | p-Chlorophenol | .050 | 98.6 | 95.9 |
| 17 | p-Chloroacetopheonone | .200 | 100.0 | 96.8 |
| 18 | Benzoyl Chloride | .050 | 98.0 | 94.8 |

Runs 14 and 18 were carried out in toluene and all the others were carried out using isopropanol as the solvent. Although runs 11, 13 and 15 resulted in stereoselectivities slightly less than the preferred minimum limit of 92% these runs are still within the scope of the present invention.

EXAMPLE 5

A series of tests was conducted to determine the effect of sulfur level in d-trans-piperitol. In these tests, a W. R. Grace and Co. Raney nickel catalyst "Raney 30" was treated with 7.5% $NiCl_2 \cdot 6H_2O$ as in Example 1. Hydrogenation was carried out for about 22.5 hours. With 40-50 parts per million sulfur, a conversion of 61.8% was obtained producing 4.8% d-menthol and 95.3% d-isomenthol. Stereoselectivity was slightly increased to 96.1% at 32 parts per million and to 96.5% with 21 parts per million. Optimum conversion of 94% producing 2.3% d-menthol and 97.6% d-isomenthol was obtained with 0 parts per million sulfur.

EXAMPLE 6

This example illustrates the improved results obtained employing other nickel catalysts. The following table illustrates results obtained:

TABLE 5

| Catalyst | Modifier/% | Conversions, %/Time, Hrs. | % Stereoselectivity d-Iso |
|---|---|---|---|
| Raney 28 | $NiCl_2$/7.5 | 100/12 | 99.0 |
| Raney 28 | $NiCl_2$/7.5 | 100/20.5 | 98.6 |
| Raney 30 | $NiCl_2$/7.5 | 99.5/22.5 | 97.4 |
| A-5000 | $NiCl_2$/7.5 | 99/21.5 | 97.1 |
| Girdler G-69 | None | 95.4/4.5 | 93.5 |
| Girdler G-69 | $CuCl_2$/2 | 99/11 | 97.0 |

The "Raney 28" and "Raney 30" catalysts were manufactured by W. R. Grace and Co. and the "A-5000" catalyst was manufactured by Activated Metals, Inc. Catalyst treatment was only with the catalyst modifier at 23° C for 30 minutes; except in the case with Girdler G-69 wherein the catalyst was first activated in isopropanol with hydrogen at 400 – 500 psig. for 1–2 hours before adding the d-trans-piperitol to the cooled (25° C) slurry of catalyst. Hydrogenation was carried out with 10 grams d-transpiperitol, 10 grams isopropanol, and 0.4 grams catalyst at room temperature and at 50–60 psig hydrogen. The results achieved with A-5000 nickel catalyst and Raney 30 catalyst are within the scope of the present invention, as is that with modified G-69.

The above examples were all carried out with pretreatment of the catalyst with one or more of the stated modifier compounds. It is possible, as a substitute to pretreatment, to use the modifier compounds as direct additives to the hydrogenation reaction mixture, as in method (B) of Example 3. However, the additive method requires that the amount of modifier added be optimized to obtain equivalent stereoselectivity, and accordingly, pretreatment of the catalyst may preferred.

EXAMPLE 7

This example illustrates applicability of the invention to the hydrogenation of other monocyclic alcohols. In this example, cis- and trans- isopiperitenols were hydrogenated as a mixture. d-cis-isopiperitenol yielded on hydrogenation an amount of l-neoisomenthol and a predominant amount of d-neomenthol, whereas l-trans-isopiperitenol yielded an amount of l-menthol and a predominant amount of l-isomenthol. Analysis was by vapor phase chromatography. Two reactions were conducted, both with Raney nickel catalyst, one in which the catalyst was treated with 0.375 grams $NiCl_2 \cdot 6H_2O$ per gram of catalyst. The following results were obtained;

TABLE 6

| Run | Catalyst Modifier | % Conv. | % Stereoselectivity d-Neo[5] | 1-Iso[6] |
|---|---|---|---|---|
| 1 | None | 100 | 80.0 | 84.5 |
| 2 | $NiCl_2 \cdot 6H_2O$ | 100 | 95.2 | 97.4 |

[5] % d-Neomenthol = $\dfrac{100 \cdot [\text{d-Neomenthol}]}{[\text{d-Neomenthol}] + [\text{l-Neoisomenthol}]}$

[6] % l-Isomenthol = $\dfrac{100 \cdot [\text{l-Isomenthol}]}{[\text{l-Isomenthol}] + [\text{l-Menthol}]}$ In a still further example, l-cis-piperitol was hydrogenated to yield an amount of d-neoisomenthol and a predominant amount of l-neomenthol, as follows:

TABLE 7

| Run | Modifier | Hrs. | % Conv. | % 1-neo[7] |
|---|---|---|---|---|
| 1 | none | 6.0 | 75 | 86.8 |
| 2 | $NiCL_2 \cdot 6H_2O$ | 3.5 | 56 | 94.0 |

TABLE 7-continued

| Run | Modifier | Hrs. | % Conv. | % 1-neo[7] |
|---|---|---|---|---|

[7] $\%\ 1\text{-Neomenthol} = \dfrac{100.\ [1\text{-Neomenthol}]}{[1\text{-Neomenthol}] + [d\text{-Neoisomenthol}]}$

What is claimed is:

1. In a process for hydrogenation, with elemental hydrogen gas in the presence of a hydrogenation catalyst, under hydrogenation conditions, of a cyclic unsaturated compound having a hydroxyl group projecting from an asymmetric center of the ring and an olefinic carbon-to-carbon double bond which when saturated in the hydrogenation process creates in additional asymmetric center in the ring, the improvement for obtaining increased stereoselectivity by increasing the addition of said hydrogen to that side of the olefinic bond on the same side of the compound molecule as said hydroxyl group, wherein said hydrogenation is conducted with a nickel hydrogenation catalyst that has an effective fraction of its reactive surfaces inactivated by treating said catalyst with an effective amount of a modifier selected from the group consisting of: an inorganic salt of a metal from Groups I through VIII, Periods 4 through 7 of the Periodic Table, of the Rare Earths of the Periodic Table, and of aluminum; organic halides; hydrogen halides; and halo compounds or arsenic and boron.

2. The process of claim 1 wherein said cyclic unsaturated compound is a terpene carbocyclic alcohol.

3. The process of claim 2 wherein said hydroxyl group is allylic to the olefinic carbon-to-carbon double bond.

4. The process of claim 3 wherein said cyclic unsaturated compound is d-trans-piperitol, the hydrogenation product being predominantly d-isomenthol.

5. The process of claim 1 wherein said hydrogenation catalyst is a Raney nickel catalyst.

6. The process of claim 1 wherein said catalyst is pretreated with a solution of the modifier prior to carrying out the hydrogenation, said pretreatment comprising stirring the modifier solution and catalyst together for a period of time sufficient to obtain said inactivation and then removing excess modifier solution.

7. The process of claim 1 wherein said modifier is added directly to the reaction mixture of catalyst and cyclic unsaturated compound prior to hydrogenation, the amount of modifier being about 0.01 – 100% based on the weight of the catalyst.

8. The process of claim 4 wherein, said d-trans-piperitol contains sulfur and is desulfurized prior to hydrogenation.

9. The process of claim 1 wherein said catalyst has a substantial fraction of its reactive surfaces inactivated by treating said catalyst with a modifier selected from the group consisting of $NiCl_2$ and $CuCl_2$.

10. In a process for hydrogenation, with elemental hydrogen gas in the presence of a hydrogenation catalyst under hydrogenation conditions, of d-trans-piperitol, the improvement for obtaining increased stereoselectivity in the synthesis of d-isomenthol wherein said hydrogenation is conducted with a nickel hydrogenation catalyst that has an effective fraction of its reactive surfaces inactivated, said inactivation being carried out by pretreating the catalyst with an effective amount of a modifier selected from the group consisting of: an inorganic salt of a metal from Groups I through VIII, Periods 4 through 7 of the Periodic Table, of the Rare Earths of the Periodic Table, and of aluminum; organic halides; hydrogen halides; and halo compounds of arsenic and boron.

11. The process of claim 10 wherein said catalyst is pretreated with a solution of the modifier prior to carrying out the hydrogenation, said pretreatment comprising stirring the modifier solution and catalyst together for a period of time sufficient to obtain said inactivation and then removing excess modifier.

12. The process of claim 10 wherein said modifier is added directly to the reaction mixture of catalyst and cyclic unsaturated compound prior to hydrogenation, the amount of modifier being about 0.01 – 100% based on the weight of the catalyst.

13. The process of claim 11 wherein said d-trans-piperitol contains sulfur and is desulfurized prior to hydrogenation.

* * * * *